(12) United States Patent
Eastman et al.

(10) Patent No.: US 6,691,554 B2
(45) Date of Patent: Feb. 17, 2004

(54) NANOCRYSTALLINE FILMS FOR GAS-REACTIVE APPLICATIONS

(75) Inventors: Jeffrey A. Eastman, Naperville, IL (US); Loren J. Thompson, Minooka, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 09/833,168

(22) Filed: Apr. 11, 2001

(65) Prior Publication Data

US 2002/0148278 A1 Oct. 17, 2002

(51) Int. Cl.[7] .............................................. G01N 25/18
(52) U.S. Cl. ................... 73/25.03; 73/25.03; 73/31.06; 73/23.2; 422/95; 338/34
(58) Field of Search ............................ 73/25.03, 31.06, 73/23.2; 422/95; 338/34

(56) References Cited

U.S. PATENT DOCUMENTS

| 4,243,631 | A | * | 1/1981 | Ryerson .................... 324/71.5 |
| 4,369,647 | A | * | 1/1983 | Shigemori et al. .......... 340/634 |
| 4,387,359 | A | * | 6/1983 | Tien et al. .................... 338/34 |
| 4,510,036 | A | * | 4/1985 | Takeuchi et al. ............ 204/408 |
| 4,574,264 | A | * | 3/1986 | Takahashi et al. ............ 338/34 |
| 4,880,519 | A | * | 11/1989 | Wang et al. ................. 204/425 |
| 5,128,081 | A | * | 7/1992 | Siegel et al. ................. 264/115 |
| 5,535,614 | A | | 7/1996 | Okamoto et al. |
| 5,644,068 | A | | 7/1997 | Okamoto et al. |
| 5,728,195 | A | * | 3/1998 | Eastman et al. ............ 264/430 |
| 5,821,402 | A | * | 10/1998 | Okajima et al. .............. 422/90 |
| 6,134,946 | A | * | 10/2000 | Liu et al. .................... 73/31.06 |
| 6,265,222 | B1 | * | 7/2001 | DiMeo et al. ................ 422/83 |
| 6,406,181 | B1 | * | 6/2002 | Mueller et al. ............ 73/25.03 |

* cited by examiner

*Primary Examiner*—Hezron Williams
*Assistant Examiner*—André K. Jackson
(74) *Attorney, Agent, or Firm*—Emrich and Dithmar

(57) ABSTRACT

A gas sensor for detection of oxidizing and reducing gases, including $O_2$, $CO_2$, CO, and $H_2$, monitors the partial pressure of a gas to be detected by measuring the temperature rise of an oxide-thin-film-coated metallic line in response to an applied electrical current. For a fixed input power, the temperature rise of the metallic line is inversely proportional to the thermal conductivity of the oxide coating. The oxide coating contains multi-valent cation species that change their valence, and hence the oxygen stoichiometry of the coating, in response to changes in the partial pressure of the detected gas. Since the thermal conductivity of the coating is dependent on its oxygen stoichiometry, the temperature rise of the metallic line depends on the partial pressure of the detected gas. Nanocrystalline (<100 nm grain size) oxide coatings yield faster sensor response times than conventional larger-grained coatings due to faster oxygen diffusion along grain boundaries rather than through grain interiors.

55 Claims, 3 Drawing Sheets

NANOCRYSTALLINE FILMS FOR GAS-REACTIVE APPLICATIONS

The United States Government has rights in this invention pursuant to Contract No. W-31-109-ENG-38 between the U.S. Department of Energy and The University of Chicago representing Argonne National Laboratory.

FIELD OF THE INVENTION

This invention relates generally to sensors for use in gas-reactive applications and is particularly directed to the detection of oxidizing and reducing gases using changes in the thermal conductivity of a solid oxide thin film arising from oxygen partial pressure dependent changes in the defect content of the film.

BACKGROUND OF THE INVENTION

Oxygen sensors are the most widely used type of gas sensor, and are employed in applications related to personal safety, industrial process control, and environmental protection, to name just a few. As one example of their widespread usage, oxygen sensors are used in all modern automobiles to provide exhaust emission feedback control, as well as to monitor the performance of components such as the fuel injection system, the exhaust gas recirculation valve, and the catalytic converter. Multiple sensors can be present in a single vehicle.

A common type of oxygen sensor operates on the principle of solid-state electrolysis. Both amperometric (based on measurement of an electrical current through an electrolyte) or potentiometric (based on measurement of a voltage) styles exist. The most common sensor design used for automotive applications is called the Heated Exhaust Gas Oxygen (HEGO) Sensor. A schematic of this type of potentiometric sensor 10 is shown in FIG. 1. A zirconia thimble 12 is used as the electrolyte, which separates the gaseous exhaust region being monitored from a sealed reference region that contains a gas with a known oxygen partial pressure (typically air). A ceramic heater 20 is disposed within and extends substantially the entire length of the zirconia thimble 12. Porous platinum coatings 14, 16 respectively disposed on the inner and outer thimble surfaces serve as inner and outer electrodes. An electromotive force (EMF) develops when the sensor 10 is exposed to an exhaust gas with a $pO_2$ that differs from that of the reference gas due to the development of different oxygen vacancy concentrations in the electrolyte near the two electrolyte-electrode interfaces.

Undesirable features associated with the HEGO-type sensor 10 shown in FIG. 1 include (1) the need for a reference gas region; (2) the relatively complex design that includes the bulk zirconia thimble 10 (the electrolyte) with a geometry that increases production costs; (3) the need for a metallic shield 18 to prevent contact with and possible breakage of the zirconia thimble; (4) possible reproducibility issues associated with the processing and use of porous electrodes (the electrode must provide electrical continuity, but at the same time be porous to allow gas to contact the electrolyte); and (5) the relative insensitivity of the sensor to changing $pO_2$ except very near the stoichiometric gas ratio of $pCO/pO_2$ or $pH_2/pO_2=2$, where a large step-wise change in EMF occurs.

U.S. Pat. Nos. 5,644,068 and 5,535,614 disclose a gas sensor of the thermal conductivity type for use in the quantitative analysis of fuel vapor content of a fuel-air mixture. This approach measures the thermal conductivity of the gas being sampled for the purpose of determining a composition of the gas mixture. Because the thermal conductivity of oxygen and nitrogen gases are almost identical, this type of thermal conductivity sensor could not be used in detecting the partial pressure of a gas such as oxygen in air or in a nitrogen-containing gas mixture. U.S. Pat. No. 4,369,647 is directed to a gas leakage detector which includes a solid state gas sensor having a sintered metallic oxide block which changes its thermal conductivity by chemical absorption thereto and a wire for transforming thermal conductivity changes into an electric signal. The solid state gas sensor is described as including a non-oxidizable metal wire such as of platinum which is coated with a sintered block of metallic oxide such as of $SnO_2$. This gas leakage detector is not disclosed as sensing a partial gas pressure from one component in a gas mixture, nor is there any suggestion that the gas leakage detector could be used for sensing oxidizing and reducing gas species. The disclosed gas leakage detector is described in terms of detecting the leakage of a gas containing methane, liquid petroleum, nitrous oxide, and fluoroethylene.

The present invention addresses the aforementioned limitations of the prior art by providing a gas sensor which detects the presence of an oxidizing or reducing gas by measurements of oxygen partial gas pressure-dependent changes in solid oxide thin film thermal conductivity. These changes in thermal conductivity arise due to changes in the defect content of the thin film in response to changes in oxygen partial pressure. Compared to the HEGO-type sensor, the inventive gas sensor (1) eliminates the need for a reference gas; (2) has a simpler design by using thin films rather than bulk machined ceramics; (3) is more damage-tolerant due to the elimination of the zirconia thimble; (4) places the oxide coating in direct contact with the environment being sensed rather than buried under a porous electrode; and (5) allows the pressure regime over which maximum sensitivity is obtained to be controlled by controlling the type(s) of cation dopants.

OBJECTS AND SUMMARY OF THE INVENTION

Accordingly, it is an object of the present invention to provide a gas sensor employing a thin film for detecting the presence of an oxidizing or reducing gas.

It is another object of the present invention to provide for the fast detection of a gas using a nanocrystalline oxide coating based upon the faster diffusion of oxygen along grain boundaries than through grain interiors as in conventional larger-grained sensor coatings.

Yet another object of the present invention is to provide for the selective detection of plural gas species using plural thin film coatings disposed on an electrical conductor and having varying permeability.

A further object of the present invention is to provide a sensor which detects the presence of an oxidizing or reducing gas by measurement of the partial gas pressure-dependent changes in the thermal conductivity of a solid oxide thin film.

The present invention contemplates a gas sensor for detecting an oxidizing or reducing gas, such as $O_2$, $CO_2$, CO, $NH_3$ or $H_2$. Monitoring of a partial pressure of a gas to be detected is accomplished by measuring the amplitude of the temperature oscillations of an oxide-thin-film-coated metallic line in response to an applied variable frequency electrical current. For a fixed input power, the magnitude of the temperature rise in the metallic line is inversely proportional to the thermal conductivity of the oxide coating. The oxide coating contains multi-valent cation species that change their valence, and thus the oxygen stoichiometry of the coating, in response to changes in the partial pressure of the detected gas. Because the thermal conductivity of the thin oxide coating is dependent on oxygen stoichiometry, the temperature rise of the metallic line depends on the partial pressure of the detected gas. Upon detection of an oxidizing gas, the thermal conductivity of the oxide thin film increases, allowing the thin film to transport more heat away from the underlying metallic line. This causes the temperature of the metallic line to decrease, which is measured as a corresponding drop in the amplitude of the voltage oscillations in the metallic line. Detection of a reducing gas leads to an opposite effect. The thermal conductivity of the oxide thin film decreases, resulting in a reduction in the amount of heat that the thin film can absorb from the metallic conductor. This causes the metallic conductor's temperature to rise, which is measured as a rise in the amplitude of the voltage oscillations in the metallic line. Measurement of thermal conductivity, and hence the partial pressure of the detected gas, employs either a modification of the three omega ($3\omega$) technique or a new method described below. Nanocrystalline (<100 nm grain size) oxide coatings yield faster sensor response times than conventional larger-grained coatings due to faster oxygen diffusion along grain boundaries rather than through grain interiors. The use of a nanoporous oxide coating further improves sensor response time and reduces sensor operating temperature. Gas species may be selectively detected through the use of additional coatings with varying permeability.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

DETAILED DESCRIPTION OF THE PREFERRED EMBODIMENTS

Figure 1:
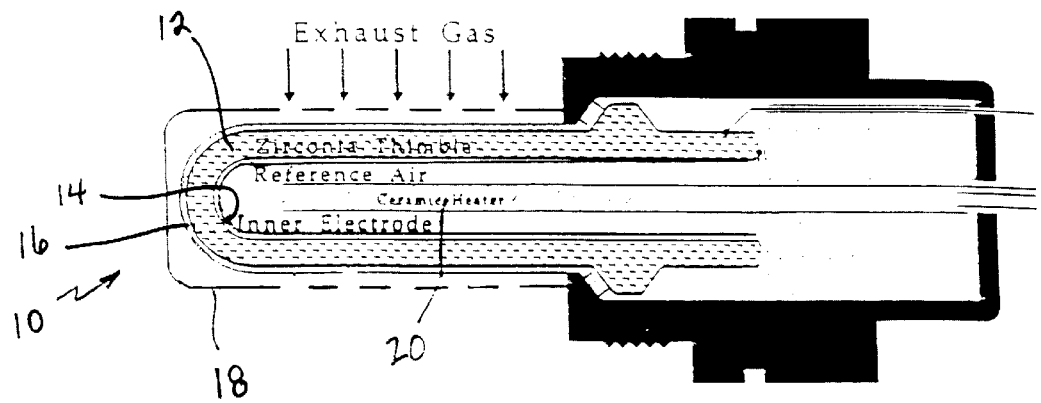
FIG. 1 is a longitudinal section view of a conventional Heated Exhaust Gas Oxygen (HEGO) potentiometric sensor such as used in automotive applications.
Figure 2:
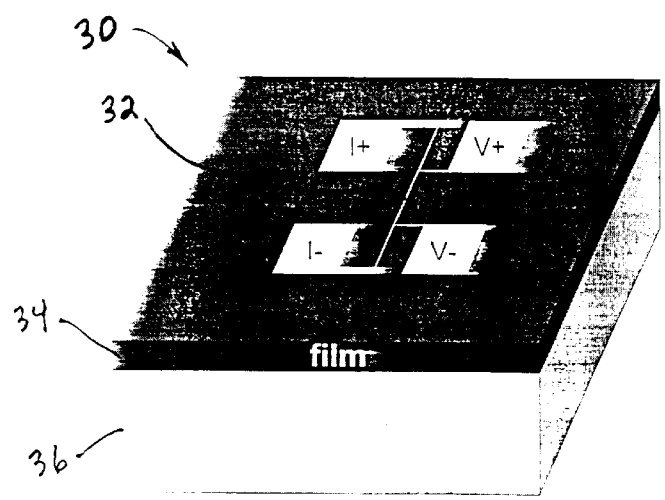
FIG. 2 is a simplified schematic view of a gas sensor incorporating a nanocrystalline film for measuring $3\omega$ thermal conductivity in accordance with one embodiment of the present invention.
Figure 3:
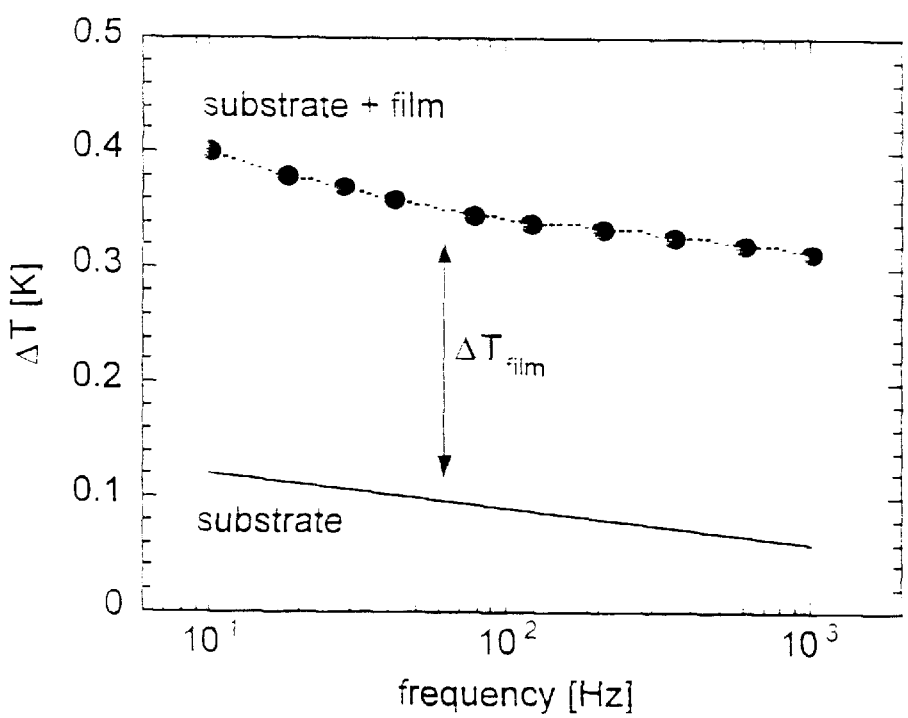
FIG. 3 is a graphic representation of the frequency dependence of the temperature rise of a metallic line as used in the present invention.

Referring to FIG. 2. there is shown apparatus 30 for detecting the presence of a gas in accordance with one embodiment of the present invention. Apparatus 30 uses the $3\omega$ method for measuring thermal conductivity of a thin film 34 deposited on a substrate 36. Apparatus 30 uses a lithographically-patterned metal line (typically gold on chromium) 32 that functions as both heater and thermometer when a current is passed through it. The line is patterned onto the surface of a thin film 34 grown on substrate 36. An AC-current of frequency $\omega$ is passed between two current contacts I$^+$ and I$^-$ on the thin metal line 32. Two voltage contacts V$^+$ and V$^-$ connected to the metal line 32 allow the voltage across the metal line 32 to be measured. The AC-current of frequency $\omega$ heats the metal line 32 at a frequency $2\omega$. Since the resistance of the metal line 32 changes with temperature, the temperature oscillations at the surface of the sample produce an oscillation of the electrical resistance at a frequency $2\omega$. Consequently, the voltage drop across the metal line 32, which is the product of current times resistance, has a small component at $3\omega$. This voltage can be used to measure the amplitude of the temperature oscillations, $\Delta T$, of the metal line 32, which is assumed to be equal to the temperature oscillations at the surface of the thin film 34. In cases where the thin film 34 has a small thermal conductivity compared to that of the substrate 36 and the film thickness is small compared to the thermal penetration depth, the thin film adds a frequency-independent component to the temperature oscillations observed for an uncoated substrate. By measuring the frequency dependence of $\Delta T$ as shown in FIG. 3, the thermal conductivity of both the thin film and the underlying substrate can be determined simultaneously. FIG. 3 shows graphically the measured $\Delta T$ at room temperature for an approximately 800 nm thick amorphous-SiO$_2$ coating on a Si substrate. The thermal conductivity of the substrate is proportional to the slope $\partial \ln\omega / \partial \Delta T$, while the thermal conductivity of the thin film is proportional to $1/\Delta T_{film}$, where $1/\Delta T_{film}$ is the difference in the temperature rise of the metal line on a coated or uncoated substrate. The thermal conductivity is thus determined from measurements of the voltage oscillations at $3\omega$. The $3\omega$ method is particularly well-suited for measuring the thermal conductivity of thin films and is sensitive to very small amplitude temperature oscillations. It has been used successfully with films as thin as 20 nm and with temperature oscillations <0.1 K.

In accordance with the present invention, the oxygen-vacancy-dependent thermal conductivity of solid oxides such as zirconia is used to sense changes in the partial pressure of a detected gas. The high temperature cubic phase of zirconia exists over a wide stoichiometric range and can be stabilized to low temperatures by alloying with aliovalent cation species. For example, at room temperature, cubic yttria-stabilized zirconia (YSZ) is stable for yttria concentrations from approximately 8 mol. % Y$_2$O$_3$ to >30 mol. % Y$_2$O$_3$. The thermal conductivity of YSZ is known to depend on the yttria concentration, with larger yttria concentrations yielding smaller thermal conductivity values. This behavior is believed to arise due to the effect of yttria concentration on the oxygen vacancy concentration in the thin film. To maintain charge neutrality, for each two Y$^{3+}$ ions substituting for two Zr$^{4+}$ ions, one oxygen vacancy must be created. Calculations indicate that increasing the Y$_2$O$_3$ concentration in YSZ from 7 wt. % to 20 wt. % results in a reduction in thermal conductivity by approximately 25–30% at any temperature from 20° C. to 1200° C.

Since the thermal conductivity of cubic zirconia varies with oxygen vacancy concentration, changing the valence of a multivalent stabilizing cation atom should have a similar effect on thermal conductivity as changing the aliovalent cation concentration.

For example, cerium can exist in either +3 ($Ce_2O_3$) or +4 ($CeO_2$) valences. A cubic ceria-stabilized zirconia sample would change thermal conductivity in response to a change in the partial pressure of a detected gas such as oxygen because the fraction of cerium ions in +3 or +4 valence states (and hence the oxygen vacancy concentration) will vary with the gas partial pressure.

Multivalent cation stabilizers or solutes in zirconia other than cerium produce similar effects (e.g., iron can exist in +2 and +3 valences and titanium can exist in +2 and +4 valences, to give just a few examples). Oxides other than zirconia with wide stoichiometric ranges and multi-valent cations such as cerium oxide could also be used to produce partial gas pressure-dependent changes in thermal conductivity.

Figure 4:
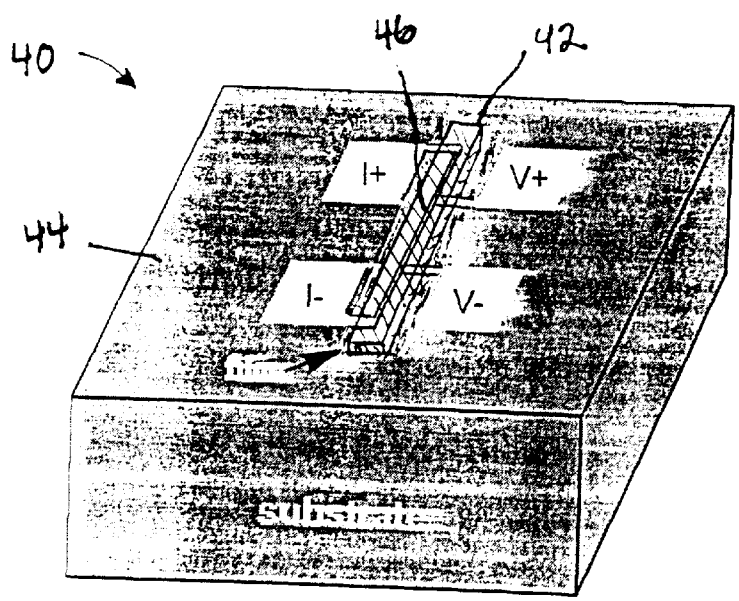
FIG. 4 is a simplified schematic view of another embodiment of a gas sensor in accordance with the present invention, wherein the metal heater-thermometer is disposed under an oxide coating.

As described above, the 3ω method is an effective technique for measuring the thermal conductivity of oxide thin films. The configuration of the apparatus 30 shown in FIG. 2, however, is not ideal for gas sensing purposes since the oxide film is buried under the metal heater/thermometer. For gas sensing, the heater/thermometer metallic line could be porous, as is the case for the electrodes in the HEGO sensor. Alternatively, a dense metallic line could be used instead, such as shown in FIG. 4 which is described in detail below. Similar geometries have been previously employed when using the (3ω) technique to measure the thermal conductivity of liquids.

Referring to FIG. 4, there is shown a simplified schematic view of a sensor for use in the 3ω thermal conductivity measurement for gas sensing in accordance with the present invention. Apparatus 40 includes an elongated, linear metal line 46 disposed on the surface of a substrate 44. An oxide coating thin film 42 is deposited on the surface of the substrate 44 and over the metal line 46. $I^+$ and $I^-$ contacts connected to opposed ends of the metal line 46 permit an electric current to be induce in the metal line by means of a current source (not shown for simplicity). The voltage drop along the length of the metal line 46 may be measured by means of a spaced voltage contacts V+ and V– contacts connected to the metal line in combination with a volt meter (also not shown in the figures for simplicity). Metal line 46 is thus disposed under the oxide coating thin film 42. In this arrangement, heat flow is in two directions in the metal line 46 and data analysis is modified accordingly. Heat flows either down into the substrate 44 or up into the thin film 42.

A full 3ω measurement requires the use of a lock-in amplifier to produce the drive current and detect the third-harmonic voltage. If one were interested in manufacturing gas sensors operating on the thermal conductivity ideas described herein, it would be undesirable to require the use of a relatively expensive lock-in amplifier. However, since the ΔT associated with the thin film is independent of frequency, it is possible to obtain the required information with inexpensive electronics that use only a single drive frequency. A full 3ω measurement could be performed as part of the manufacturing process in order to calibrate the sensor and ensure that the expected $\partial \ln\omega/\partial\Delta T$ behavior is observed.

Figure 5:
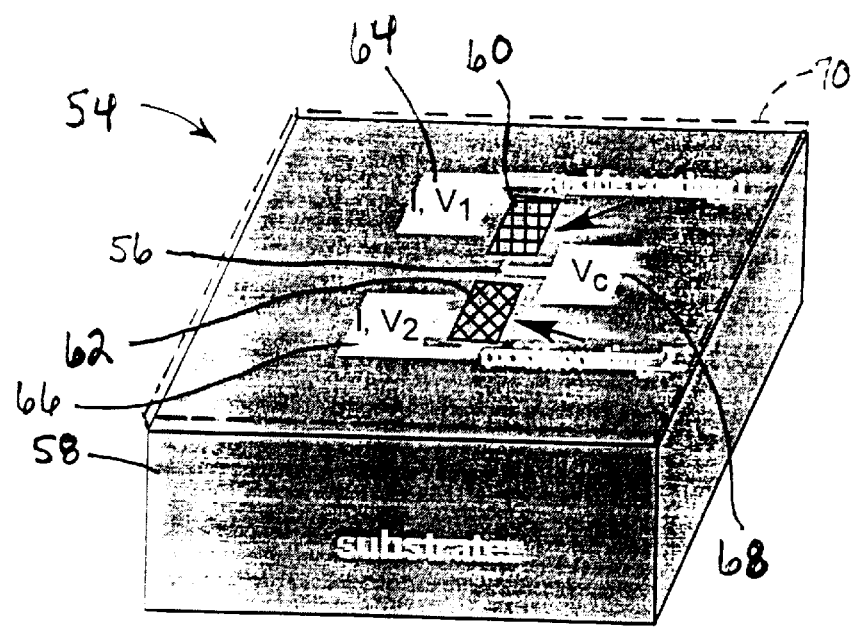
FIG. 5 is a simplified schematic view of yet another embodiment of a gas sensor in accordance with the present invention, wherein one oxide coating contains multi-valent cations, while a second oxide coating is insensitive to changes in oxygen partial pressure.

Since the measured quantity needed for gas sensing purposes is the change in thermal conductivity with change in the partial pressure of the detected gas rather than the actual thermal conductivity value, the present invention contemplates another embodiment as shown in FIG. 5. FIG. 5 is a simplified schematic view of another apparatus 54 for measuring the thermal conductivity of a thin metal line 56 representing a measure of the partial pressure of a detected gas in accordance with another embodiment of the present invention. Apparatus 54 includes a substrate 58 upon which the thin metal line 56 is deposited. First and second thin oxide coatings 60 and 62 are deposited upon respective portions of metal line 56. One of the oxide coatings contains multi-valent cations, while the other oxide coating is insensitive to the partial pressure of the detected gas. A first terminal 64 is disposed on the substrate 58 and electrically connected to one end of the metal line 56 and is adapted for connection to one terminal of a current source such as an alternating electric current at frequencies in the range of from 10 Hz to 10,000 Hz as well as to a volt meter for measuring a first voltage $B_1$. A second terminal 66 is also disposed on the substrate 58 and is electrically connected to a second, opposed end of the metal line 56 and is adapted for connection to a second terminal of the current source as well as to the voltmeter for measuring $V_2$ at the second end of the metal line. A third terminal 68 disposed on the substrate 58 is electrically connected to an intermediate portion of the metal line 56 at a location between the first and second thin film oxide coatings 60, 62. because the voltage difference between $V_1$ and $V_c$, or between $V_2$ and $V_c$ depends on the temperature of the metal line between those points and that temperature depends on the thermal.

The embodiment of the invention shown in FIG. 5 is also envisioned in a modification that would provide selective detection of one among plural gas species by adding an additional top coating 70 (shown in dotted line form) on the sensor, the coating being permeable to some gas species, but impermeable to others. For example, adding a palladium layer on top of the thin oxide coating containing multi-valent cations would result in a measurable response if this type of sensor were exposed to the reducing gas hydrogen, but no response if the same sensor were exposed to the reducing gas carbon monoxide. This selective behavior would arise because palladium is highly permeable to hydrogen at all envisioned sensor operating temperatures, while palladium is impermeable to transport of carbon monoxide at envisioned sensor operating temperatures.

Fast response times (≦1 sec) are desired for most gas sensors, such as, for example, in oxygen sensor applications. In the case of potentiometric sensors, operating temperatures of 500° C. or higher are often used to ensure rapid electromotive force (EMF) equilibration. The response time is aided by the fact that only the concentration of oxygen vacancies within a small number of atomic spacings of the electrode-electrolyte interfaces are important in determining the EMF in the present invention. Diffusion through the bulk zirconia thimble as in the above described prior approach is not required.

In the case of the thermal conductivity-based sensor of the present invention, the rate limiting step that determines the sensor response time to a change in gas partial pressure is likely the oxygen transport rate through the oxide film. There are several strategies that can be used to minimize the response time. First, an oxide coating with a large oxygen self-diffusion coefficient should be used (e.g., zirconia, ceria, or bismuth oxide). If a film thickness of x=100 nm is assumed and a response time of t=1 sec is desired, the required minimum oxygen diffusion coefficient, D, can be calculated from $D=x^2/t$ to be approximately $10^{-16}$ $m^2$/sec. For comparison, the estimated oxygen diffusion coefficient for cubic YSZ is approximately $10^{-13}$ $m^2$/sec at 500° C. Lower temperature diffusion data have not been measured, but it is clear that expected sensor operating temperatures of significantly less than 500° C. should be achievable with rapid response times.

Reducing the oxide film thickness below 100 nm also improves sensor response time. However, since the ΔT measured by the 3ω technique is directly proportional to the film thickness, there is a trade-off between optimizing the sensor sensitivity and response time (a thinner film will respond faster, but will have a smaller ΔT for a given change in partial gas pressure).

Controlling the oxide grain size to be nanocrystalline (<100 nm) provides significant increases in oxygen transport rate due to the faster diffusion rates along grain boundaries compared to diffusion through the bulk. For example, the oxygen diffusion coefficient in nanocrystalline monoclinic zirconia is approximately 4 orders of magnitude larger than the bulk oxygen diffusion coefficient in coarse-grained samples. Increasing the oxygen transport rate also makes low operating temperatures feasible.

It is possible that under some conditions the rate limiting step in determining sensor response time could be the rate at which $O_2$ molecules crack and are adsorbed into the oxide film. Processing of the sensor oxide coating to have a nanocrystalline microstructure with average grain size less than 200 nm is also an advantage here. It has been demonstrated that nanocrystalline oxides exhibit high catalytic activity. For example, nanocrystalline cerium oxide shows greatly enhanced catalytic activity for CO oxidation compared to coarser-grained microstructures. CO can be oxidized at temperatures as low as 80° C. on nanocrystalline cerium oxide. Improved catalytic activity may facilitate more rapid changes in oxygen content in nanocrystalline oxide films compared to oxide films with grain size larger than 200 nm. Improved catalytic activity may also facilitate changes in oxygen content in oxide thin films at lower temperatures.

Since the present invention is sensitive to the partial pressure of the detected gas rather than the specific oxidizing or reducing gas species (as is also the case for existing potentiometric and amperometric oxygen sensors), the present invention contemplates additional techniques for the selective detection of one among plural gas species. For example, for distinguishing between the reducing gases $H_2$ and CO two sensors could be employed simultaneously, one with and one without an additional top thin film of palladium. Since hydrogen has very high permeability through palladium while CO does not, the Pd-coated and uncoated sensors would respond similarly when exposed to hydrogen but differently when exposed to carbon monoxide. Similar types of permeable or non-permeable membranes could be developed to provide selectivity between other gas species. This embodiment of the invention could be implemented in the configuration shown in FIG. 5 where one thin film disposed over the metal line is sensitive to the presence of a first gas and a second thin film is sensitive to the presence of a second gas.

While particular embodiments of the present invention have been shown and described, it will be obvious to those skilled in the relevant art that changes and modifications may be made without departing from the invention in its broader aspects. Therefore, the aim in the appended claims is to cover all such changes and modifications as fall within the true spirit and scope of the invention. The matter set forth in the foregoing description in accompanying drawings is offered by way of illustration only and not as a limitation. The actual scope of the invention is intended to be defined in the following claims when viewed in their proper perspective based on the prior art.

The embodiments of the invention in which an exclusive property or privilege is claimed are defined as follows:

1. A gas sensor for detecting an oxidizing or reducing gas comprising:
    a thin metal electrical conductor having an electric current therein, wherein the temperature of said conductor oscillates in response to said electric current; and
    a first thin oxide coating disposed in contact with said electrical conductor, said first thin oxide coating containing one or more multi-valent cation species that change valence and hence the oxygen content of said first thin oxide coating in response to a change in a partial pressure of a detected gas giving rise to a change in thermal conductivity of said first thin oxide coating, and wherein the temperature oscillations in said electrical conductor change with a change in thermal conductivity of said first thin oxide coating providing an indication of the presence of said detected gas.

2. The gas sensor of claim 1, wherein the amount of detected gas present is quantified by measurement of the magnitude of the temperature oscillations in said electrical conductor.

3. The gas sensor of claim 1, wherein said first thin coating is comprised of zirconia alloyed with a multi-valent cation species.

4. The gas sensor of claim 3, wherein said multi-valent cation species is yttrium.

5. The gas sensor of claim 1, wherein said first thin coating is comprised of cubic yttria-stabilized zirconia.

6. The gas sensor of claim 5, wherein said multi-valent cation species is cerium.

7. The gas sensor of claim 1, wherein said first thin coating is comprised of cubic ceria-stabilized zirconia.

8. The gas sensor of claim 1, wherein said first thin oxide coating is comprised of cubic yttria-stabilized zirconia alloyed with plural multi-valent cation species.

9. The gas sensor of claim 8, wherein said plural multi-valent cation species include iron or titanium.

10. The gas sensor of claim 1, wherein said first thin oxide coating is comprised of ceria.

11. The gas sensor of claim 1, wherein said first thin oxide coating is comprised of ceria alloyed with iron or titanium.

12. The gas sensor of claim 1, wherein said first thin oxide coating is comprised of ceria-stabilized zirconia alloyed with iron or titanium.

13. The gas sensor of claim 1, wherein said first thin coating is disposed on a substrate and said electrical conductor is disposed on said first thin coating.

14. The gas sensor of claim 13, wherein said electrical conductor is porous to allow contact of the detected gas species with said first thin oxide coating.

15. The gas sensor of claim 13, further comprising first and second current contacts electrically coupled to said electrical conductor in a spaced manner for providing an electric current thereto.

16. The gas sensor of claim 15, wherein said first and second current contacts are disposed on said first thin oxide coating.

17. The gas sensor of claim 16, further comprising first and second voltage contacts electrically coupled to said electrical conductor intermediate the connections of said electrical conductor to said first and second current contacts.

18. The gas sensor of claim 17, wherein said first and second voltage contacts are disposed on said first thin oxide coating.

19. The gas sensor of claim 1, wherein said electrical conductor is disposed on a substrate and said first thin oxide coating is disposed on said electrical conductor.

20. The gas sensor of claim 19 further comprising first and second current contacts electrically coupled to said electrical conductor in a spaced manner for providing an electric current thereto.

21. The gas sensor of claim 20, wherein said first and second current contacts are disposed on said substrate.

22. The gas sensor of claim 21 further comprising first and second voltage contacts electrically coupled to said electrical conductor intermediate the connections of said electrical conductor to said first and second current contacts.

23. The gas sensor of claim 22, wherein said first and second voltage contacts are disposed on said substrate.

24. The gas sensor of claim 1 further comprising a second thin gas-permeable or gas impermeable coating disposed on said electrical conductor for detection of a gas among plural gas species.

25. The gas sensor of claim 24, wherein said second coating is permeable to hydrogen gas, but impermeable to carbon monoxide.

26. The gas sensor of claim 25, wherein said second coating is comprised of palladium.

27. The gas sensor of claim 1, wherein said electric current is either direct current or alternating current applied to the said electrical conductor at a single frequency.

28. The gas sensor of claim 27, wherein the thermal conductivity of said first thin oxide coating is determined in a quantitative manner.

29. The gas sensor of claim 27, wherein said alternating electric current is applied to the said electrical conductor at frequencies in the range of 10 Hz to 10,000 Hz.

30. The gas sensor of claim 27, wherein said alternating electric current is applied to the said electrical conductor at a single frequency.

31. The gas sensor of claim 30, wherein the change in thermal conductivity of said first thin oxide coating in response to a change in concentration of said detected gas is determined in a quantitative manner.

32. The gas sensor of claim 19 further comprising:
a second thin oxide coating disposed on said electrical conductor in a spaced manner from said first thin oxide coating, wherein said second thin oxide coating is insensitive to the presence of said detected gas;
and a voltage measuring arrangement connected to said electrical conductor for measuring a first voltage in said electrical conductor adjacent said first thin oxide coating and a second voltage in said electrical conductor adjacent said second thin oxide coating, wherein a voltage difference between said first and second voltages indicates the presence of a detected gas.

33. The gas sensor of claim 32, wherein the amount of detected gas present is quantified by measurements of the magnitude of the voltage difference between said first and second voltages.

34. The gas sensor of claim 32, wherein said voltage measuring arrangement includes first and second voltage contacts electrically coupled to said electrical conductor in a spaced manner and a third voltage contact coupled to said electrical conductor intermediate said first and second voltage contacts.

35. The gas sensor of claim 33, further comprising first and second current contacts electrically coupled to said electrical conductor in a spaced manner for providing an electric current thereto, wherein said first current and first voltage contacts are collocated and said second current and second voltage contacts are collocated.

36. The gas sensor of claim 35, wherein said current and voltage contacts are disposed on said substrate.

37. The gas sensor of claim 32, wherein said first thin oxide coating is comprised of magnesium oxide alloyed with iron and said second thin oxide coating is comprised of magnesium oxide.

38. The gas sensor of claim 32, wherein said first thin oxide coating is comprised of magnesium oxide alloyed with titanium and said second thin oxide coating is comprised of magnesium oxide.

39. The gas sensor of claim 32, wherein said first thin oxide coating is comprised of magnesium oxide alloyed with cerium and said second thin oxide coating is comprised of magnesium oxide.

40. The gas sensor of claim 33, further comprising a third thin gas-permeable or gas impermeable coating disposed on said first thin oxide coating for selective detection of one among plural gas species.

41. The gas sensor of claim 40, wherein said third thin coating is permeable to hydrogen gas, but impermeable to carbon monoxide.

42. The gas sensor of claim 40 wherein said third thin coating is comprised of palladium.

43. The gas sensor of claim 40, wherein said alternating electric current is applied to the said electrical conductor at plural frequencies.

44. The gas sensor of claim 41, wherein said alternating electric current is applied to the said electrical conductor at frequencies in the range of 10 Hz to 10,000 Hz.

45. The gas sensor of claim 44, wherein the thermal conductivity of said first and second thin oxide coatings is determined in a quantitative manner.

46. The gas sensor of claim 40, wherein said alternating electric current is applied to the said electrical conductor at a single frequency.

47. The gas sensor of claim 46, wherein the change in thermal conductivity of said first thin oxide coating in response to a change in concentration of said detected gas is determined in a quantitative manner.

48. A gas sensor for detecting an oxidizing or reducing gas comprising: a thin metal electrical conductor having an electric current therein, wherein the temperature of said conductor oscillates in response to said electric current; and a first thin oxide coating disposed in contact with said electrical conductor, said thin oxide coating containing one or more multi-valent cation species that change valence and hence the oxygen content of said thin oxide coating in response to a change in a partial pressure of a detected gas giving rise to a change in thermal conductivity of said thin oxide coating and wherein said first thin oxide coating is nanocrystalline with a grain size less than approximately 200 nm for providing faster response times and lower sensor operating temperatures when exposed to changes in detected gas concentration,
wherein the temperature oscillations in said electrical conductor change with a change in thermal conductivity of said thin oxide coating providing an indication of the presence of said detected gas.

49. A method for detecting an oxidizing or reducing gas comprising providing a gas sensor in contact with the oxidizing or reducing gas, the gas sensor including
a thin metal electrical conductor having an electric current therein, wherein the temperature of said conductor oscillates in response to said electric current; and
a first thin oxide coating disposed in contact with said electrical conductor, said thin oxide coating containing one or more multi-valent cation species that change valence and hence the oxygen content of said thin oxide coating in response to a change in a partial pressure of a detected gas giving rise to a change in thermal conductivity of said thin oxide coating, and wherein the temperature oscillations in said electrical conductor change with a change in thermal conductivity of said thin oxide coating providing an indication of the presence of said detected gas.

50. The method set forth in claim 49, wherein the gas sensor has electrical conductors disposed on the substrate and the first thin oxide coating is disposed on the electrical conductor and is permeable to a first gas, or gas impermeable coating disposed on the electrical conductor for detection of a gas among a plurality of gas species, the second coating being permeable to hydrogen gas but impermeable to carbon monoxide.

51. The method of claim 49, wherein the second coating is palladium and the first coating is a nanocrystalline oxide with a grain size less than approximately 200 nm.

52. A gas sensor for detecting an oxidizing or reducing gas comprising:

a thin metal electrical conductor having an electric current therein, wherein the temperature of said conductor oscillates in response to said electric current; and a first oxide coating disposed in contact with said electrical conductor, said first thin oxide coating containing one or more multi-valent cation species that change valence and hence the oxygen content of said first oxide coating in response to a change in a partial pressure of a detected gas giving rise to a change in thermal conductivity of said first oxide coating, wherein the temperature oscillations in said electrical conductor change with a change in thermal conductivity of said first oxide coating, and mechanism sensing the change in thermal conductivity of the oxide coating providing an indication of the presence of said detected gas.

53. A method of detecting the presence of a gas using the gas sensor of claim 51.

54. The method of claim 50, wherein said first and second detected gases are carbon monoxide and hydrogen.

55. The method of claim 49, wherein selective detection of carbon monoxide or hydrogen is provided.

* * * * *

UNITED STATES PATENT AND TRADEMARK OFFICE
CERTIFICATE OF CORRECTION

PATENT NO.    : 6,691,554 B2
DATED         : February 17, 2004
INVENTOR(S)   : Jeffrey A. Eastman et al.

It is certified that error appears in the above-identified patent and that said Letters Patent is hereby corrected as shown below:

Column 6,
Line 40, delete " $\underset{=}{\leq}$ " and insert -- $\leq$ --.

Signed and Sealed this

Thirty-first Day of August, 2004

JON W. DUDAS
*Director of the United States Patent and Trademark Office*